US00PP15312P2

(12) United States Plant Patent
Kievit

(10) Patent No.: US PP15,312 P2
(45) Date of Patent: Nov. 16, 2004

(54) ***FUCHSIA* PLANT NAMED 'KIEFUDIB'**

(50) Latin Name: *Fuchsia×hybrida*
Varietal Denomination: Kiefudib

(75) Inventor: Christa Kievit, Venhuizen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/787,020

(22) Filed: Feb. 25, 2004

(51) Int. Cl.[7] ..... A10H 5/00
(52) U.S. Cl. ..... Plt./300
(58) Field of Search ..... Plt./300

(56) References Cited

PUBLICATIONS

UPOV–ROM GTITM, Plant Variety Database, GTI Jouve Retrieval Software, Citation for *Fuchsia* 'Kiefudib'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Fuchsia* plant named 'Kiefudib', characterized by its compact and upright growth habit; freely branching habit; dense and full plant habit; light red and white-colored flowers; and freely and continuous flowering habit.

1 Drawing Sheet

Botanical classification/cultivar designation: *Fuchsia×hybrida* cultivar Kiefudib.

BACKGROUND OF THE INVENTION

The present invention relates to a new and distinct cultivar of *Fuchsia* plant, botanically known as *Fuchsia×hybrida,* and hereinafter referred to by the name 'Kiefudib'.

The new *Fuchsia* is a product of a planned breeding program conducted by the Inventor in Venhuizen, The Netherlands. The objective of the breeding program was to create new *Fuchsia* cultivars with an upright and compact plant habit, numerous flowers and attractive flower coloration.

The new *Fuchsia* originated from a cross-pollination made by the Inventor during the early winter of 1999 of a proprietary selection *Fuchsia×hybrida* identified as code number 3134-2, not patented, as the female, or seed, parent with a proprietary selection *Fuchsia×hybrida* identified as code number 3134-1, not patented, as the male, or pollen, parent. The cultivar Kiefudib was discovered and selected by the Inventor as a flowering plant within the resulting progeny of the stated cross-pollination in a controlled environment in Venhuizen, The Netherlands.

Asexual reproduction of the new *Fuchsia* by terminal cuttings at Venhuizen, The Netherlands, since the summer of 1999 has shown that the unique features of this new *Fuchsia* are stable and reproduced true to type in successive generations.

BRIEF SUMMARY OF THE INVENTION

The cultivar Kiefudib has not been observed under all possible environmental conditions. The phenotype may vary somewhat with variations in environment such as temperature and daylength, without, however, any variance in genotype.

The following traits have been repeatedly observed and are determined to be the unique characteristics of 'Kiefudib'.

These characteristics in combination distinguish 'Kiefudib' as a new and distinct *Fuchsia* cultivar:

1. Compact and upright growth habit.
2. Freely branching habit; dense and full plant habit.
3. Light red and white-colored flowers.
4. Freely and continuous flowering habit.

Compared to plants of the female parent selection, plants of the new *Fuchsia* have darker green-colored leaves. Plants of the new *Fuchsia* are more upright than male parent selection differ in flower coloration.

Plants of the new *Fuchsia* can be compared to plants of the cultivar Pink, not patented. In side-by-side comparisons conducted in Venhuizen, The Netherlands, plants of the new *Fuchsia* differed primarily from plants of the cultivar Pink in the following characteristics:

1. Plants of the new *Fuchsia* were more freely flowering than plants of the cultivar Pink.
2. Plants of the new *Fuchsia* flowered earlier and more continuously than plants of the cultivar Pink.
3. Plants of the new *Fuchsia* had darker pink-colored sepals than plants of the cultivar Pink.
4. Plants of the new *Fuchsia* were more tolerant to wind and rain than plants of the cultivar Pink.

BRIEF DESCRIPTION OF THE PHOTOGRAPHS

The accompanying colored photographs illustrate the overall appearance of the new *Fuchsia*, showing the colors as true as it is reasonably possible to obtain in colored reproductions of this type. Colors in the photographs may differ slightly from the color values cited in the detailed botanical description which accurately describe the colors of the new *Fuchsia.*

The photograph at the top of the sheet comprises a side perspective view of a typical potted plant of 'Kiefudib'.

The photograph at the bottom sheet is a close-up view of typical developing flowers, opened flowers and leaves of 'Kiefudib'.

DETAILED BOTANICAL DESCRIPTION

The aforementioned photographs and following observations and measurements describe plants grown in Lompoc, Calif., under commercial practice during the summer and early fall in a polycarbonate-covered greenhouse with day temperatures about 21 to 27° C., night temperatures about 16 to 18° C., and light levels about 5,000 to 9,000 foot-candles. One cutting was planted per 10-cm container and plants were grown for about 13 weeks. In the following description, color references are made to The Royal Horticultural Society Colour Chart, 1995 Edition, except where general terms of ordinary dictionary significance are used.

Botanical classification: *Fuchsia×hybrida* cultivar Kiefudib.

Parentage:

*Female or seed parent.*—Proprietary selection of *Fuchsia×hybrida* identified as code number 3134-2, not patented.

*Male, or pollen, parent.*—Proprietary selection of *Fuchsia×hybrida* identified as code number 3134-1, not patented.

Propagation:

*Type cutting.*—Terminal cuttings.

*Time to initiate roots, summer and winter.*—About 14 days at 21° C.

*Time to produce a rooted cutting.*—Summer: About 28 days at 21° C. Winter: About 32 days at 21° C.

*Root description.*—Fine, fibrous and white in color.

*Rooting habit.*—Freely-branching.

Plant description:

*Form.*—Upright growth habit, relatively compact and freely branching habit; dense and full plants. Freely flowering. Appropriate for 10 to 15-cm containers. Moderately vigorous.

*Plant height at flowering.*—About 24 cm.

*Plant diameter at flowering.*—About 26 cm.

*Branching habit.*—Freely branching; typically seven lateral branches develop per plant. Pinching (removal of terminal apex) enhances lateral branch development.

*Lateral branch description.*—Length: About 20 cm. Diameter: About 3 mm. Internode length: About 2.3 cm. Aspect: Upright. Strength: Strong. Texture: Slightly pubescent. Color: 182B.

*Foliage description.*—Arrangement: Opposite, simple. Length: About 4 cm. Width: About 1.8 cm. Shape: Elliptic to lanceolate. Apex: Acute. Base: Obtuse. Margin: Entire with minute points; undulate. Texture, upper and lower surfaces: Smooth, glabrous. Venation pattern: Pinnate, arcuate. Petiole length: About 1.25 cm. Petiole diameter: About 2 mm. Petiole texture, upper and lower surfaces: Smooth, glabrous. Color: Developing leaves, upper surface: 137C. Developing leaves, lower surface: 146B. Fully expanded leaves, upper surface: 147A. Fully expanded leaves, lower surface: 147B. Venation, upper surface: 147B. Venation, lower surface: 147C. Petiole, upper and lower surfaces: 146C.

Flower description:

*Flower type and habit.*—Single bi-colored axillary flowers. Freely and flowering; potentially two flowers per leaf axil; about four open flowers and about eight to ten flower buds per lateral branch. Flowers not persistent. Flowers not fragrant.

*Natural flowering season.*—April through October in northern Europe; flowering continuous during this period.

*Flower longevity.*—Flowers last about seven to ten days on the plant.

*Flower orientation.*—Initially upright, then pendulous.

*Flower diameter.*—About 4.7 cm.

*Flower height.*—About 6.3 cm.

*Flower buds.*—Shape: Elongated. Length: About 4.7 cm. Width: About 1.2 cm. Color: Towards the base, 55C; mid-section, 56C; towards the apex, 155A; at apex, 144D.

*Petals.*—Quantity: Four; imbricate. Length: About 2.2 cm. Width: About 2 cm. Shape: Fan-shaped. Apex: Rounded. Margin: Entire. Texture, upper and lower surfaces: Glabrous, smooth and velvety. Color: When opening, upper and lower surfaces: 155C. Fully opened, upper and lower surfaces: More white than 155D; towards base, 62C.

*Sepals.*—Quantity: Four; fused at base. Length: About 2.8 cm. Width: About 8 mm. Aspect: Mostly flat. Shape: Elliptic. Apex: Acuminate. Margin: Entire. Texture, upper and lower surfaces: Glabrous, smooth, waxy. Color, when opening and fully opened, upper and lower surfaces: 55B; towards the apex, 55C to 55D.

*Peduncles.*—Length: About 2.5 cm. Diameter: About 1.5 mm. Aspect: About 45 to 60° from the stem. Strength: Moderately strong. Texture: Smooth, glabrous. Color: 144A.

*Reproductive organs.*—Stamens: Stamen number: Eight per flower. Anther length: About 3 mm. Anther diameter: About 2 mm. Anther shape: Oblong. Anther color: 64B. Filament length: About 9.3 cm. Filament color: Close to 66D. Pollen amount: Moderate. Pollen color: 158A. Pistils: Pistil number: One per flower. Pistil length: About 6 cm. Style length: About 4.8 cm. Style color: 49D. Stigma shape: Ovate. Stigma color: 158A. Ovary color: 144A.

*Seed/fruit.*—Seed and fruit production has not been observed.

Disease/pest resistance: Plants of the new *Fuchsia* have not been observed to be resistant to pathogens and pests common to *Fuchsias*.

Temperature tolerance: Plants of the new *Fuchsia* have been observed to tolerate low temperatures of 10° C. and high temperatures of 30° C.

Garden performance: Plants of the new *Fuchsia* perform have been observed to perform well in the garden and are tolerant to rain and wind.

It is claimed:

1. A new and distinct cultivar of *Fuchsia* plant named 'Kiefudib', as illustrated and described.

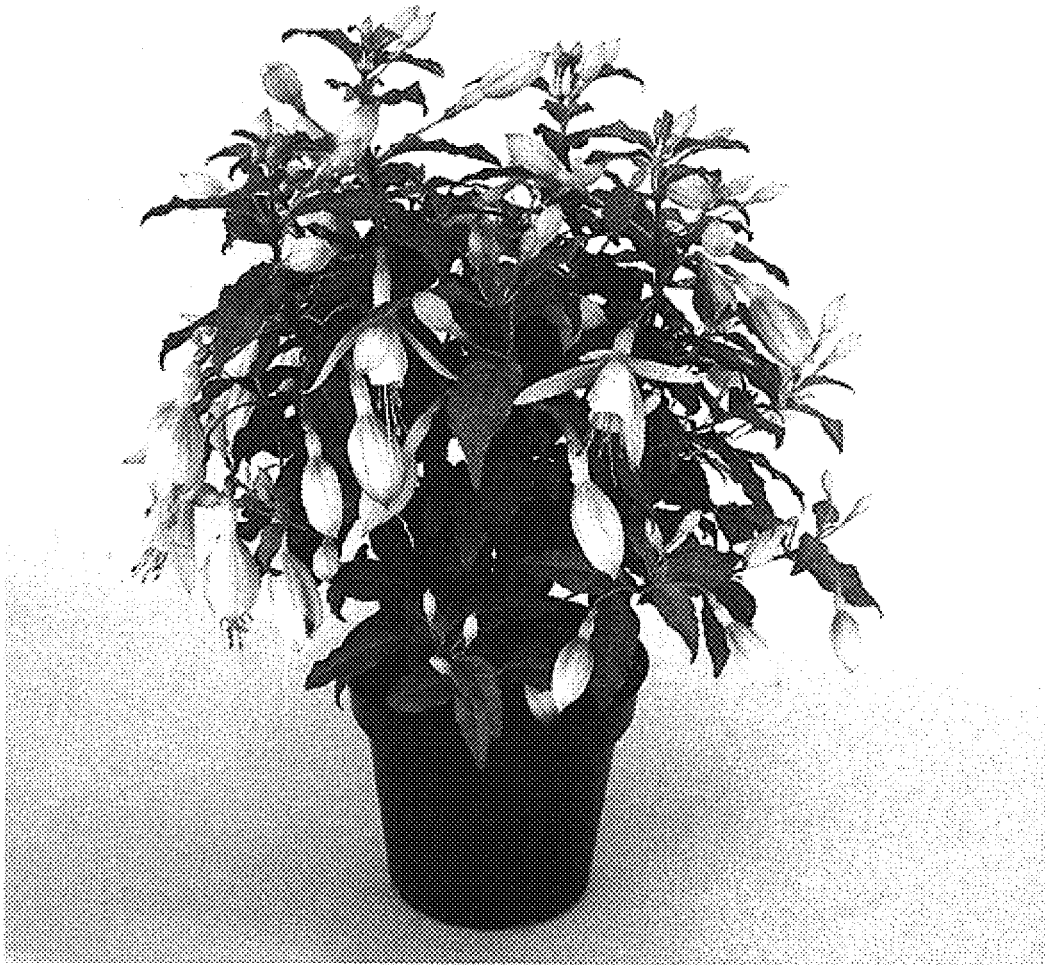
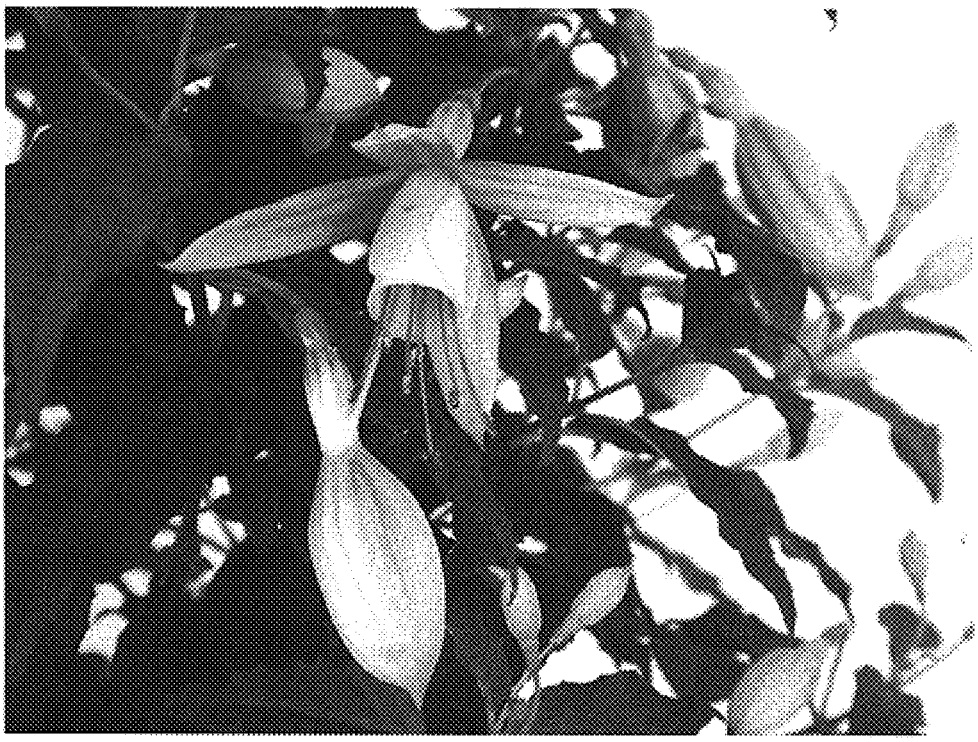

* * * * *